United States Patent
Dharmakumar

(10) Patent No.: US 10,471,094 B2
(45) Date of Patent: Nov. 12, 2019

(54) METHODS FOR REDUCING ISCHEMIA-REPERFUSION INJURY VIA TARGETED CONTROL OF BLOOD GASES

(71) Applicant: Cedars-Sinai Medical Center, Los Angeles, CA (US)

(72) Inventor: Rohan Dharmakumar, Moorpark, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 713 days.

(21) Appl. No.: 14/909,922

(22) PCT Filed: Aug. 5, 2014

(86) PCT No.: PCT/US2014/049832
§ 371 (c)(1),
(2) Date: Feb. 3, 2016

(87) PCT Pub. No.: WO2015/021078
PCT Pub. Date: Feb. 12, 2015

(65) Prior Publication Data
US 2016/0166606 A1    Jun. 16, 2016

Related U.S. Application Data

(60) Provisional application No. 61/862,211, filed on Aug. 5, 2013.

(51) Int. Cl.
*A61M 16/00* (2006.01)
*A61K 33/00* (2006.01)
*A61F 7/12* (2006.01)
*A61M 16/12* (2006.01)

(52) U.S. Cl.
CPC .............. *A61K 33/00* (2013.01); *A61F 7/12* (2013.01); *A61M 16/00* (2013.01); *A61M 16/12* (2013.01); *A61F 2007/126* (2013.01)

(58) Field of Classification Search
CPC combination set(s) only.
See application file for complete search history.

(56) References Cited

U.S. PATENT DOCUMENTS

| | | | |
|---|---|---|---|
| 5,670,177 A | 9/1997 | Briend et al. | |
| 5,975,748 A | 11/1999 | East, IV et al. | |
| 6,013,243 A | 1/2000 | Achilefu | |
| 6,951,216 B2 | 10/2005 | Heinonen | |
| 7,073,501 B2 | 7/2006 | Remmers et al. | |
| 7,941,204 B1 | 5/2011 | Wang et al. | |
| 8,290,226 B2 | 10/2012 | Gühring et al. | |
| 8,936,777 B2 | 1/2015 | Cesati et al. | |
| 2002/0103454 A1 | 8/2002 | Sackner et al. | |
| 2002/0185129 A1 | 12/2002 | Fisher et al. | |
| 2003/0017612 A1 | 1/2003 | Gerber et al. | |
| 2004/0081623 A1 | 4/2004 | Eriksen et al. | |
| 2004/0167467 A1 | 8/2004 | Harrison et al. | |
| 2004/0206354 A1 | 10/2004 | Fisher et al. | |
| 2005/0124907 A1 | 6/2005 | Kuck et al. | |
| 2005/0165311 A1 | 7/2005 | Porter et al. | |
| 2005/0228337 A1 | 10/2005 | Rasor et al. | |
| 2006/0100639 A1* | 5/2006 | Levin ............... | A61M 25/10182 606/106 |
| 2006/0239524 A1 | 10/2006 | Desh et al. | |
| 2006/0264755 A1 | 11/2006 | Maltz et al. | |
| 2007/0014764 A1 | 1/2007 | Levy et al. | |
| 2007/0043409 A1* | 2/2007 | Brian, III ................ | A61F 7/12 607/105 |
| 2007/0169779 A1* | 7/2007 | Freeman ............... | A61M 16/12 128/204.18 |
| 2007/0287897 A1 | 12/2007 | Faris et al. | |
| 2008/0171933 A1 | 7/2008 | Li et al. | |
| 2010/0086483 A1 | 4/2010 | Belardinelli et al. | |
| 2010/0168649 A1 | 7/2010 | Schwartz et al. | |
| 2010/0240983 A1 | 9/2010 | Jung et al. | |
| 2010/0305459 A1 | 12/2010 | Whitt et al. | |
| 2011/0184384 A1 | 7/2011 | Davalian et al. | |
| 2014/0053837 A1 | 2/2014 | Klein | |
| 2014/0088406 A1 | 3/2014 | Dharmakumar et al. | |
| 2014/0170069 A1 | 6/2014 | Dharmakumar et al. | |
| 2014/0311491 A1* | 10/2014 | Klein ..................... | A61B 5/083 128/204.22 |
| 2015/0196207 A1 | 7/2015 | Friedrich et al. | |

(Continued)

FOREIGN PATENT DOCUMENTS

| | | |
|---|---|---|
| AU | 2012250539 A1 | 12/2013 |
| CA | 2845308 A1 | 11/2012 |
| CA | 2832851 A1 | 5/2015 |

(Continued)

OTHER PUBLICATIONS

PCT/US2014/049832 International Search Report and Written Opinion dated Nov. 6, 2014; 8 pages.
Mutch et al. Cerebral Oxygen Saturation: Graded Response to Carbon Dioxide with Isoxia and Graded Response to Oxygen with Isocapnia. PLoS One (2013). 8(2):e57881; 7 pages.
PCT/US2014/049832 International Preliminary Report on Patentability dated Feb. 18, 2016; 8 pages.
International Search Report and Written Opinion for PCT/US2012/036813 dated Aug. 7, 2012, 9 pages.

(Continued)

*Primary Examiner* — Joseph A Stoklosa
*Assistant Examiner* — Adam J Avigan
(74) *Attorney, Agent, or Firm* — Linda B. Huber; Nixon Peabody LLP

(57) ABSTRACT

Provided herein are methods for reducing ischemia-reperfusion injury and/or microvascular obstructions by administering to the subject effective amounts of carbon dioxide and oxygen before, during and/or after re-establishing perfusion. In some embodiments, the methods further include using therapeutic hypothermia.

20 Claims, No Drawings

(56) References Cited

U.S. PATENT DOCUMENTS

| | | |
|---|---|---|
| 2018/0185519 A1 | 7/2018 | Dharmakumar et al. |
| 2019/0038781 A1 | 2/2019 | Dharmakumar et al. |

FOREIGN PATENT DOCUMENTS

| | | | |
|---|---|---|---|
| EP | 2704577 A1 | | 3/2014 |
| WO | WO 2000/057776 A1 | | 10/2000 |
| WO | WO 2000/78774 A2 | | 12/2000 |
| WO | WO 2001/64280 A1 | | 9/2001 |
| WO | WO 2007/084264 A2 | | 7/2007 |
| WO | WO 2008/122056 A2 | | 10/2008 |
| WO | WO 2010/033971 A1 | | 3/2010 |
| WO | WO 2010/141081 A2 | | 12/2010 |
| WO | 2012149226 A2 | | 11/2012 |
| WO | 2012151583 A1 | | 11/2012 |
| WO | WO 2012/149226 A2 | | 11/2012 |
| WO | WO 2012/151583 | * | 11/2012 |
| WO | WO 2012/151583 A1 | | 11/2012 |
| WO | 2015021078 A1 | | 2/2015 |

OTHER PUBLICATIONS

International Preliminary Report on Patentability for PCT/US2012/036813 dated Jun. 11, 2013, 8 pages.
International Search Report and Written Opinion for PCT/US2012/035307 dated Aug. 3, 2012, 9 pages.
International Preliminary Report on Patentability for PCT/US2012/035307 dated Nov. 7, 2013.
EP 12779635.7 Extended Search Report dated Sep. 17, 2014, 7 pages.
Abdel-Aty et al., Delayed enhancement and T2-weighted cardiovascular magnetic resonance imaging differentiate acute from chronic myocardial infarction. Circulation, 2004. 109(20): p. 2411-6.
Akca, O. Optimizing the intraoperative management of carbon dioxide concentration. Curr Opin Anasthesiol 2006; 19:19-25.
Atalay M, Reeder SB, Zerhouni E, Forder Jr. Blood Oxygenation Dependence of T1 and T2 in the Isolated, Perfused Rabbit Heart at 4.7T. Magn Reson Med. 1995;34:623-627.
Back et al., Angiography with Carbon Dioxide (CO2), Surgical Clinics of North America, 1998, vol. 78(4), pp. 575-591.
Baddeley et al. Gas exchange parameters in radiotherapy patients during breathing of 2%, 3.5% and 5% carbogen gas mixtures. Br J Radiol. 2000;73:1100-1104.
Baron et al. Independent role of arterial o2 tension in local control of coronary blood flow. Am J Physiol. 1990;258:H1388-1394.
Battisti-Chalbonney et al., The cerebrovascular response to carbon dioxide in humans. J Physiol. 2011. 589:3039-3048.
Beaudin et al. Cerebral and myocardial blood flow responses to hypercapnia and hypoxia in humans. Am J Physiol Heart Circ Physiol. 2011;301:H1678-1686.
Blockley et al. Measuring venous blood volume changes during activation using hyperoxia. Neuroimage. 2012;59:3266-3274.
Bondarenko et al. Standardizing the definition of hyperenhancement in the quantitative assessment of infarct size and myocardial viability using delayed contrast-enhanced CMR. J Cardiovasc Magn Reson. 2005;7:481-485.
Brandi et al., The Role of Carbon Dioxide Therapy in the Treatment of Chronic Wounds, In Vivo, 2010, vol. 24(2), pp. 223-226.
Braunwald E. Acute myocardial infarction. Heart disease: A textbook of cardiovascular medicine. Philadelphia ; London: Saunders; 1997:1184-1288.
Carr et al. Cine MR angiography of the heart with segmented true fast imaging with steady-state precession. Radiology. Jun. 2001;219(3):828-34.
Case et al. The response of canine coronary vascular resistance to local alterations in coronary arterial p co2. Circ Res. 1976;39:558-566.
Costa et al., Quantitative magnetic resonance perfusion imaging detects anatomic and physiologic coronary artery disease as measured by coronary angiography and fractional flow reserve. J Am Coll Cardiol. 2007;50:514-522.
Dharmakumar et al., Blood Oxygen-Sensitive SSFP Imaging for Probing the Myocardial Perfusion Reserves of Patients with Coronary Artery Disease: A Feasibility Study. SCMR 2008 (Los Angeles, USA).
Duruble et al. Transient responses of coronary flow in the blood-perfused isolated rat heart submitted to changes in oxygen content. J Physiol. 1985;358:321-334.
Dutton et al., Carbon Dioxide and Liver Blood Flow, Bull. Europ. Physiopath. Resp., 1976, 12, 265-272.
Edelman RR, Li W. Contrast-Enhanced Echo-Planar MR imaging of Myocardial Perfusion: Preliminary Study in Humans Radiology. 1994;190:771-777.
Feigl EO. Coronary physiology. Physiol Rev. 1983;63:1-205.
Fierstra et al. End-inspiratory rebreathing reduces the end-tidal to arterial pco2 gradient in mechanically ventilated pigs. Intensive care medicine. 2011;37:1543-1550.
Foex et al. Effect of co2 on the systemic and coronary circulations and on coronary sinus blood gas tensions. Bull Eur Physiopathol Respir. 1979;15:625-638.
Glenny RW, Bernard S, Brinkley M. Validation of fluorescent-labeled microspheres for measurement of regional organ perfusion. J Appl Physiol. 1993;74:2585-2597.
Gotberg et al., A Pilot Study of Rapid Cooling by Cold Saline and Endovascular Cooling Before Reperfusion in Patients With ST-Elevation Myocardial Infarction, Cir. Cardiovasc. Interv., 2010, 3(5): 400-7.
Hachamovitch et al., Comparison of the short-term survival benefit associated with revascularization compared with medical therapy in patients with no prior coronary artery disease undergoing stress myocardial perfusion single photon emission computed tomography. Circulation. 2003;107:2900-2907.
Hale et al., Hypothermia during reperfusion limits 'no-reflow' injury in a rabbit model of acute myocardial infarction, Cardiovascular Research, 2003, 59(3):715-722.
Hale et al., Mild Hypothermia as a Cardioprotective Approach for Acute Myocardial Infarction: Laboratory to Clinical Application, Journal of Cardiovascular Pharmacology and Therapuetics, 2010, vol. 16(2), pp. 131-139.
Han et al. Impact of extracranial-intracranial bypass on cerebrovascular reactivity and clinical outcome in patients with symptomatic moyamoya vasculopathy. Stroke. 2011;42:3047-3054.
Harper et al. Effect of alterations in the arterial carbon dioxide tension on the blood flow through the cerebral cortex at normal and low arterial blood pressures. J Neurol Neurosurg Psychiatry. 1965;28:449-452.
Ito et al. Non-invasive prospective targeting of arterial p(co2) in subjects at rest. J Physiol. 2008;586:3675-3682.
Kachenoura et al. Evaluation of regional myocardial function using automated wall motion analysis of cine MR images: Contribution of parametric images, contraction times, and radial velocities. J Magn Reson Imaging. Oct. 2007;26(4):1127-32.
Karamitsos et al., Relationship between regional myocardial oxygenation and perfusion in patients with coronary artery disease: Insights from cardiovascular magnetic resonance and positron emission tomography. Circ Cardiovasc Imaging. 2010.3:32-40.
Kashiba et al., From O2 to H2S: a landscape view of gas biology, Keio J. Med., 2002, 51(1): 1-10.
Khan et al. Oxygen and oxygenation in stem-cell therapy for myocardial infarction. 2010 Life Sci., 87(9-10):269-274.
Kim et al. Relationship of MRI delayed contrast enhancement to irreversible injury, infarct age, and contractile function. Circulation. 1999;100:1992-2002.
Kisilevsky et al., Concentration-dependent vasoconstrictive effect of hyperoxia on hypercarbia-dilated retinal arterioles, Microvascular Research, 2008, 75, 263-268.
Klocke FJ, Simonetti OP, Judd RM, Kim RJ, Harris KR, Hedjbeli S, Fieno DS, Miller S, Chen V, Parker MA. Limits of detection of regional differences in vasodilated flow in viable myocardium by first-pass magnetic resonance perfusion imaging. Circulation. 2001;104:2412-2416.
Laffey et al. Therapeutic hypercapnia reduces pulmonary and systemic injury following in vivo lung reperfusion. Am J Respir Crit Care Med 2000;162:2287-2294.

(56) References Cited

OTHER PUBLICATIONS

Laffey et al., Effects of Therapeutic Hypercapnia on Mesenteric Ischemia-Reperfusion Injury, 2003, 168:1383-1390.

Ledingham et al. The effect of hypercapnia on myocardial blood flow and metabolism. J Physiol. 1970;210:87-105.

Mark et al. Precise control of end-tidal carbon dioxide and oxygen improves bold and asl cerebrovascular reactivity measures. Magn Reson Med. 2010;64:749-756.

Massoudy et al. Reduction of oxygen delivery during post-ischemic reperfusion protects the isolated guinea pig heart. Basic Res Cardiol 1999;94:231-237.

McCommis et al., Feasibility Study of Myocardial Perfusion and Oxygenation by Noncontrast MRI: Comparison with PET Study in a Canine Model. Magn Reson Imaging. 2008;26(1):11-19.

Midgren et al. Changes in transcutaneous pco2 with sleep in normal subjects and in patients with chronic respiratory diseases. European journal of respiratory diseases. 1987;71:388-394.

Momen et al. Coronary blood flow responses to physiological stress in humans. Am J Physiol Heart Circ Physiol. 2009;296:H854-861.

Porter et al., Myocardial perfusion imaging with contrast ultrasound. JACC Cardiovasc Imaging. 2010. 3:176-187.

Powers et al. Effect of elevations of coronary artery partial pressure of carbon dioxide (pco2) on coronary blood flow. J Am Coll Cardiol. 1986;8:1175-1181.

Prisman et al. Modified oxygen mask to induce target levels of hyperoxia and hypercarbia during radiotherapy: A more effective alternative to carbogen. Int J Radiat Biol. 2007;83:457-462.

Rong et al. Controlled oxygen reperfusion protects the lung against early ischemia-reperfusion injury in cardiopulmonary bypasses by downregulating high mobility group box 1. Experimental Lung Research 2012;38:183-191.

Sasse et al. Arterial blood gas changes during breath-holding from functional residual capacity. Chest. 1996;110:958-964.

Selimoglu et al., A Practical and Effective Approach for the Prevention of Ischemia-Reperfusion Injury after Acute Myocardial Infarcation: Pressure Regulated Lepid Blood Reperfusion, Heart Surgery Forum, 2007, vol. 10(4), pp. 309-314.

Slessarev et al. Prospective targeting and control of end-tidal co2 and o2 concentrations. J Physiol. 2007;581:1207-1219.

Spano et al. Co2 blood oxygen level-dependent mr mapping of cerebrovascular reserve in a clinical population: Safety, tolerability, and technical feasibility. Radiology. 2013;266:592-598.

St. Croix et al. Estimation of arterial pco2 in the elderly. J Appl Physiol. 1995;79:2086-2093.

Sutton et al. Left ventricular remodeling after myocardial infarction: Pathophysiology and therapy. Circulation. 2000;101:2981-2988.

Tzou et al. Coronary flow velocity changes in response to hypercapnia: Assessment by transthoracic doppler echocardiography. J Am Soc Echocardiogr. 2007;20:421-426.

van den Elshout et al., Effects of hypercapnia and hypocapnia on respiratory resistance in normal and asthmatic subjects, Thorax, 1991; 46:28-32.

Wacker et al., Changes in Myocardial Oxygenation and Perfusion Under Pharmacological Stress with Dipyridamole: Assessment Using T*2 and T1 Measurements, Magnetic Resonance in Medicine, 1999, vol. 41, pp. 686-695.

Walker et al. Salvage of skeletal muscle with free radical scavengers. J. Vasc. Surg. 1987, 5(1):68-75.

Wennmalm, A., Effect of Cigarette Smoking on Basal and Carbon Dioxide Stimulated Cerebral Blood Flow in Man, Clinical Physiology, 1982, vol. 2, pp. 529-535.

Wexels et al. Effects of carbon dioxide and ph on myocardial blood-flow and metabolism in the dog. Clin Physiol. 1985;5:575-588.

Wilke et al., Contrast-Enhanced First Pass Myocardial Perfusion Imaging: Correlation Between Myocardial Blood Flow in Dogs at Rest and During Hyperemia. Magn Reson Med. 1993;29:485-497.

Wilke et al., Myocardial Perfusion Reserve: Assessment with Multisection, Quantitative, First-Pass MR Imaging. Radiology. 1997;204:373-384.

Wise et al. Dynamic forcing of end-tidal carbon dioxide and oxygen applied to functional magnetic resonance imaging. J Cereb Blood Flow Metab. 2007;27:1521-1532.

Yokoyama et al. Heart and brain circulation and co2 in healthy men. Acta Physiol (Oxf). 2008;193:303-308.

Zhang H, Gropler RJ, Li D, Zheng J. Assessment of Myocardial Oxygen Extraction Fraction and Perfusion Reserve with BOLD Imaging in a Canine Model with Coronary Artery Stenosis. J Magn Reson Imaging. 2007;26(1):72-79.

* cited by examiner

METHODS FOR REDUCING ISCHEMIA-REPERFUSION INJURY VIA TARGETED CONTROL OF BLOOD GASES

CROSS-REFERENCE TO RELATED APPLICATIONS

This application is a National Phase of International Application No. PCT/US2014/049832 filed Aug. 5, 2014, which designated the U.S. and that International Application was published under PCT Article 21(2) in English, which claims priority under 35 U.S.C. § 119(e) to U.S. provisional patent application No. 61/862,211 filed Aug. 5, 2013, the contents of each of which are herein incorporated by reference in their entirety.

FIELD OF INVENTION

The invention is directed to methods for reducing ischemia-reperfusion injury in a subject in need thereof by delivering increased volumes of less oxygenated blood during reperfusion by controlling the delivery of oxygen and carbon dioxide in arterial blood.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Myocardial infarction (MI) or acute myocardial infarction (AMI), commonly known as a heart attack is the interruption of blood supply to a part of the heart, causing heart cells to die. Myocardial infarction is caused by ischaemic or ischemic heart disease (IHD), or myocardial ischaemia, which is characterized by reduced blood supply due to a partial or complete blockage of an artery that carries blood to the heart, usually due to coronary artery disease (atherosclerosis of the coronary arteries). The decrease in blood flow reduces the heart's oxygen supply. Myocardial ischemia is an imbalance between myocardial oxygen supply and demand. Its risk increases with, for example, age, smoking, hypercholesterolaemia (high cholesterol levels), diabetes, and hypertension (high blood pressure), and is more common in men and those who have close relatives with ischaemic heart disease. Myocardial ischemia is the pathological state underlying ischaemic heart disease.

In the event of a myocardial infarction, maximizing myocardial salvage from regions of pronounced ischemia in patients suffering an infarction is the most important goal of any therapeutic strategy delivered to the patient. The therapeutic standard for countering the acute ischemic burden is the re-establishment of blood flow, while reducing ischemia-reperfusion injury, via percutaneous transluminal coronary angioplasty (PTCA), coronary artery bypass grafting (CABG) or fibrinolysis. Of these two approaches, the most sought after therapeutic regiment is PTCA. Reperfusion therapies do not always re-establish flow and can lead to microvascular obstructions (MVOs). It has been shown that MVOs occur at the site of severe ischemic injury and that they have been associated with poor prognosis and reduced survival rates in the months and years post reperfusion. It is also known that MVOs are associated with larger infarcts and that larger infarcts lead to poorer remodeling in the chronic stage of disease culminating in heart failure. Since heart failure is a growing epidemic in the Western World, and most heart failures have origins in ischemic heart disease it is desirable to reduce ischemia-reperfusion injury in right at the acute setting.

Reperfusion can cause further damage and cell death, resulting in ischemia/reperfusion injury (IRI). There are no established drugs to prevent or treat IRI. A major cause of myocardial damage/death from IRI is a superoxide burst at reperfusion. Given the problems associated with existing reperfusion therapies, such as microvascular obstructions, there is a need in the art for reperfusion therapies that restore blood flow to the ischemic regions of the heart without any injuries to said region.

SUMMARY OF THE INVENTION

Described herein are methods for reducing and/or inhibiting ischemia-reperfusion injury in a subject in need thereof. Also described are methods for reducing or inhibiting microvascular obstructions and/or reducing hemorrhagic microvascular in a subject in need thereof.

The methods include administering to the subject a first admixture comprising carbon dioxide in an amount to achieve a predetermined partial pressure of carbon dioxide ($PaCO_2$), a second admixture comprising oxygen in an amount to achieve a predetermined partial pressure of oxygen ($PaO_2$) and re-establishing perfusion using, for example, percutaneous transluminal coronary angioplasty, CABG or fibrinolysis. The methods may further include establishing therapeutic hypothermia by cooling blood prior to reperfusion.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Route of administration" or "administering" may refer to any administration pathway known in the art, including but not limited to aerosol, nasal, oral, inhalation, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Mammal" or "subject" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathological condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Ischaemia" or "Ischemia" as used herein refers to reduced blood supply to a tissue and/or an organ. Ischemic heart disease refers to reduced blood supply to the heart due to a partial or complete blockage of an artery that carries blood to the heart.

"Reperfusion" as used herein refers to re-establishing perfusion to an ischemic area and/or organ.

"Pain to balloon time" as used herein refers to the time between the onset of symptoms of myocardial infarction up to the angioplasty.

"Effective amount" or "in an amount" as used herein refers to, for example, the amount of $O_2$ or $CO_2$ administered to the subject so as to reach a predetermined partial pressure of $O_2$ or $CO_2$, respectively.

Under normal conditions, humans breathe air that is about 21% oxygen. Current ischemia-reperfusion methods include use of 100% oxygen. The inventors hypothesize that ischemia reperfusion injury may be reduced in a subject by administering larger volumes of less oxygenated blood. This may be achieved by administering an effective amount of carbon dioxide and oxygen so as to reach predefined levels of arterial pressure of carbon dioxide and oxygen. Carbon dioxide, as a vasodilator, allows increased volumes of less oxygenated blood to be delivered to the target region.

Described herein are methods for reducing and/or inhibiting ischemia-reperfusion injury in a subject in need thereof. Also described are methods for reducing and/or inhibiting microvascular obstructions and/or reducing hemorrhagic microvascular in a subject in need thereof. The methods include administering to the subject a first admixture comprising carbon dioxide in an amount to achieve a predetermined partial pressure of carbon dioxide ($PaCO_2$), a second admixture comprising oxygen in an amount to achieve a predetermined partial pressure of oxygen ($PaO_2$) and re-establishing perfusion using, for example, percutaneous transluminal coronary angioplasty, CABG or fibrinolysis. In some embodiments, the first and second admixtures are administered concurrently. In further embodiments, the first and second admixtures are administered sequentially. In some embodiments, the oxygen source is room air. In some embodiments, the first and/or second admixtures are administered before, during and/or after percutaneous transluminal coronary angioplasty, CABG or fibrinolysis.

Also described herein are methods for reducing and/or inhibiting ischemia-reperfusion injury in a subject in need thereof. Also provided are methods for reducing and/or inhibiting microvascular obstructions and/or reducing hemorrhagic microvascular in a subject in need thereof. The methods include promoting vasidilation by administering to the subject an admixture comprising carbon dioxide in an amount to achieve a predetermined partial pressure of carbon dioxide ($PaCO_2$) and re-establishing perfusion using, for example, percutaneous transluminal coronary angioplasty, CABG or fibrinolysis. In some embodiments, in addition to $CO_2$, $O_2$ may also be administered. In an embodiment, the oxygen source is room air. In some embodiments, $CO_2$ and optionally $O_2$ are administered before, during and/or after percutaneous transluminal coronary angioplasty, CABG or fibrinolysis.

Further described are methods for reducing and/or inhibiting ischemia-reperfusion injury in a subject in need thereof. The invention also provides methods for reducing and/or inhibiting microvascular obstructions and/or reducing hemorrhagic microvascular in a subject in need thereof. The methods include administering to the subject admixture comprising oxygen in an amount to achieve a predetermined partial pressure of oxygen ($PaO_2$) and re-establishing perfusion using, for example, percutaneous transluminal coronary angioplasty, CABG or fibrinolysis. In some embodiments, in addition to $O_2$, $CO_2$ may also be administered. In an embodiment, the oxygen source is room air. In some embodiments, $O_2$ and optionally $CO_2$ are administered before, during and/or after percutaneous transluminal coronary angioplasty, CABG or fibrinolysis.

The methods described herein may further comprise establishing therapeutic hypothermia by cooling blood prior to reperfusion and/or during reperfusion. In some embodiments, establishment of reperfusion may include PTCA or fibrinolysis. Reperfusion may be established using cooled blood and concurrently or sequentially administering to the subject a first admixture comprising carbon dioxide in an amount to achieve a predetermined partial pressure of carbon dioxide ($PaCO_2$) and/or administering to the subject a second admixture comprising oxygen in an amount to achieve a predetermined partial pressure of oxygen ($PaO_2$). In some embodiments, the first and second admixtures are administered concurrently. In further embodiments, the first and second admixtures are administered sequentially.

Provided herein is a system for reducing ischemia-reperfusion injury in a subject in need thereof comprising a computerized gas control delivery systems adapted to provide a first admixture comprising carbon dioxide in an amount to reach a predetermined partial pressure of carbon dioxide to induce hyperemia and a second admixture comprising oxygen in an amount to reach a predetermined partial pressure of oxygen so as to deliver less oxygenated blood. In various embodiments, computerized gas control delivery systems include but are not limited to feedback to bend tidal gas concentration (also known as end-tidal forcing system) and prospective end-tidal targeting system (for example RespirACT™).

In some embodiments, therapeutic hypothermia is established via surface cooling of the blood or via delivering cooled blood using a catheter through the femoral artery. In various embodiments, the blood is cooled to 2-7° C. lower than the normal systemic, 2-5° C. lower than the normal systemic, 2-3° C. lower than the normal systemic, 4-7° C. lower than the normal systemic and/or 5-7° C. lower than the normal systemic. In some embodiments, the blood is cooled to temperatures described herein in myocardial infarction patients whose treatment is initiated, for example, at least 2 hours, at least 3 hours, at least 4 hour, at least 5 hours or at least 6 hours, after the onset of symptoms of myocardial infarction.

In some embodiments, symptoms of myocardial infarction include but are not limited to any one or more of chest pain, elevated FP segment in an electrocardiogram (ECG) and/or elevated troponin levels in the blood. Chest pains may be accompanied by shortness of breath, dizziness or lightheadedness, jaw pain, nausea/vomiting, unusual fatigue, cold sweat and/or pain in the arm, back, neck, abdomen, and or shoulder blades.

In some embodiments, oxygen and carbon dioxide are administered concurrently to reach pre-determined levels of partial pressures of oxygen and carbon dioxide in the arteries, during re-establishing reperfusion. In other embodiment, oxygen and carbon dioxide are administered sequentially to reach pre-determined levels of partial pressures of oxygen and carbon dioxide in the arteries, during re-establishing reperfusion. In an alternate embodiment, the subject breathes normal air concurrently with administration of carbon dioxide. In an embodiment, carbon dioxide and/or oxygen are delivered via inhalation.

In some embodiments, the extent of ischemia-reperfusion injury may be fully evaluated on the basis of MRI. Cine MRI can be used to estimate left-ventricular ejection fraction (LVEF)[1], which is a measure of global cardiac function, and estimate wall-motion anomalies[2] due to infarction. T2-weighted MRI can be used to estimate the extent of myocardial edema[3] in the acute setting and late-gadolinium enhancement MRI[4] can be used to characterize the infarction (size, location and transmurality). Collectively these measures allow one to estimate the extent IR injury at the acute, subacute and chronic phases of infarction. The extent of injury and the associated cardiac changes can also be evaluated and serially followed with other medical imaging modalities such as echocardiography, computed tomography (CT), single photon emission tomography (SPECT) and positron emission tomography.

In various embodiments, computerized gas control delivery systems may be used with the methods described herein including but not limited to feedback to bend tidal gas concentration (also known as end-tidal forcing system) and prospective end-tidal targeting system (for example RespirACT™). In some embodiments of the methods described herein, the $CO_2$ is delivered from a computerized gas control delivery system and the source of oxygen is room air. In some embodiments of the methods described herein, $O_2$ and $CO_2$ are delivered from an apparatus which includes valves that regulate the flow of the gases from the gas tanks In some embodiments, changes in breathing patterns established through voluntary (for example, by asking the subject to hold their breath for a period or hyperventilating over a period of time that is comfortable for the patient) means are used to modulate the partial pressure of $O_2$ and $CO_2$ of the blood traversing the coronary circulation.

In any organ system where ischemia is preceded by reperfusion, the proposed method is expected to reduce the tissue injury associated with re-establishment of perfusion with excessive oxygenation and suboptimal capillary recruitment. For example, the proposed method is expected to reduce ischemia-reperfusion injury in brain where treatment to resolve ongoing ischemia is mitigated via stenting of cerebral or extracaranial (carotid) arteries. Alternatively, when reperfusion is not limited to a single vessel but to whole organs (such as transplantation of heart, lungs, liver, kidney etc.), the proposed approach is expected to reduce the global injury to the transplanted organ, enhancing the long-term viability of the transplanted organ.

In some embodiments, "reduce", "reducing" and/or "reduction" of reperfusion injury as described herein refers to decrease in reperfusion injury relative to one or more reference values. In one embodiment, the reference values may be based on established standards of the scar size and/or LVEF parameters observed when the methods described herein are not used during reperfusion. In another embodiment, the reference values may be based on established standards of the scar size and/or LVEF parameters observed when 100% $O_2$ is used during reperfusion. In various embodiments, the reduction in reperfusion injury is about 10%, 20%, 30%, 40%, 50%, 60%, 70%, 80%, 90% or 100% reduction in scar size and/or LVEF relative to the reference value. In some embodiments, the percentage reduction in scar size may be about the same as the percentage reduction in LVEF. In other embodiments, the percentage reduction in scar size may be different than the percentage reduction in LVEF. In various embodiments, the reduction in reperfusion injury is about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof. In some embodiments, the fold reduction in scar size may be about the same as the fold reduction in LVEF. In other embodiments, the fold reduction in scar size may be different than the fold reduction in LVEF.

In some embodiments, the admixture comprising $CO_2$ is administered at high doses for short duration or at low doses for longer durations. For example, administering the admixture comprising $CO_2$ at high doses of $CO_2$ for a short duration comprises administering any one or more of 40 mmHg to 45 mmHg, 45 mmHg to 50 mmHg, 50 mmHg to 55 mmHg, 55 mmHg $CO_2$ to 60 mm Hg $CO_2$, 60 mmHg $CO_2$ to 65 mm Hg $CO_2$, 65 mmHg $CO_2$ to 70 mm Hg $CO_2$, 70 mmHg $CO_2$ to 75 mm Hg $CO_2$, 75 mmHg $CO_2$ to 80 mm Hg $CO_2$, 80 mmHg $CO_2$ to 85 mm Hg $CO_2$ or a combination thereof, for about 20 minutes, 15 minutes, 10 minutes, 9 minutes, 8 minutes, 7 minutes, 6 minutes, 5 minutes, 4 minutes, 3 minutes, 2 minutes, 1 minute or a combination thereof. In various embodiments, the predetermined levels of $CO_2$ are administered so that the arterial level of $CO_2$ reaches the $PaCO_2$ of any one or more of the above ranges.

For example, administering low doses of predetermined amounts of $CO_2$ for a longer duration comprises administering the predetermined amount of $CO_2$ at any one or more of about 30 mmHg $CO_2$ to about 35 mmHg $CO_2$, about 35 mmHg $CO_2$ to about 40 mmHg $CO_2$, about 40 mmHg $CO_2$ to about 45 mmHg $CO_2$ or a combination thereof for any one or more of about 20 to 24 hours, about 15 to20 hours, about 10 to 15 hours, about 5 to 10 hours, about 4 to 5 hours, about 3 to 4 hours, about 2 to 3 hours, about 1 to 2 hours, or a combination thereof, before inducing hyperemia. In various embodiments, the predetermined levels of $CO_2$ are administered so that the arterial level of $CO_2$ reaches the $PaCO_2$ of any one or more of the above ranges.

In one embodiment, $CO_2$ is administered in a stepwise manner. In another embodiment, administering carbon dioxide in a stepwise manner includes administering carbon dioxide in 5 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In another embodiment, administering carbon dioxide in a stepwise manner includes administering carbon dioxide in 10 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 20 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 30 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 40 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 50 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In some embodiments, administering oxygen in a stepwise manner includes administering oxygen in 5 mmHg increments in the range of any one or more of 30 mmHg to 100 mmHg $O_2$, 50 mmHg to 100 mmHg $O_2$, 70 mmHg to 100 mmHg $O_2$, 90 mmHg to 100 mmHg $O_2$, 30 mmHg to 200 mmHg $O_2$, 50 mmHg to 200 mmHg $O_2$, 70 mmHg to 200 mmHg $O_2$, 90 mmHg to 200 mmHg $O_2$, 150 mmHg to 200 mmHg $O_2$, 30 mmHg to 300 mmHg $O_2$, 50 mmHg to 300 mmHg $O_2$, 100 mmHg to 300 mmHg $O_2$, 150 mmHg to 300 mmHg $O_2$, 200 mmHg to 300 mmHg $O_2$, 200 mmHg to 300 mmHg $O_2$, 250 mmHg to 300 mmHg $O_2$, 30 mmHg to 400 mmHg $O_2$, 50 mmHg to 400 mmHg $O_2$, 100 mmHg to 400 mmHg $O_2$, 150 mmHg to 400 mmHg $O_2$, 200 mmHg to 400 mmHg $O_2$, 250 mmHg to 400 mmHg $O_2$, 300 mmHg to 400 mmHg $O_2$, 350 mmHg to 400 mmHg $O_2$, 30 mmHg to 500 mmHg $O_2$, 500 mmHg to 500 mmHg $O_2$, 100 mmHg to 500 mmHg $O_2$, 150 mmHg to 500 mmHg $O_2$, 200 mmHg to 500 mmHg $O_2$, 250 mmHg to 500 mmHg $O_2$, 300 mmHg to 500 mmHg $O_2$, 350 mmHg to 500 mmHg $O_2$, 400 mmHg to 500 mmHg $O_2$ or 450 mmHg to 500 mmHg $O_2$.

In some embodiments, administering oxygen in a stepwise manner includes administering oxygen in 10 mmHg increments in the range of any one or more of 30 mmHg to 100 mmHg $O_2$, 50 mmHg to 100 mmHg $O_2$, 70 mmHg to 100 mmHg $O_2$, 90 mmHg to 100 mmHg $O_2$, 30 mmHg to 200 mmHg $O_2$, 50 mmHg to 200 mmHg $O_2$, 70 mmHg to 200 mmHg $O_2$, 90 mmHg to 200 mmHg $O_2$, 150 mmHg to 200 mmHg $O_2$, 30 mmHg to 300 mmHg $O_2$, 50 mmHg to 300 mmHg $O_2$, 100 mmHg to 300 mmHg $O_2$, 150 mmHg to 300 mmHg $O_2$, 200 mmHg to 300 mmHg $O_2$, 200 mmHg to 300 mmHg $O_2$, 250 mmHg to 300 mmHg $O_2$, 30 mmHg to 400 mmHg $O_2$, 50 mmHg to 400 mmHg $O_2$, 100 mmHg to 400 mmHg $O_2$, 150 mmHg to 400 mmHg $O_2$, 200 mmHg to 400 mmHg $O_2$, 250 mmHg to 400 mmHg $O_2$, 300 mmHg to 400 mmHg $O_2$, 350 mmHg to 400 mmHg $O_2$, 30 mmHg to 500 mmHg $O_2$, 500 mmHg to 500 mmHg $O_2$, 100 mmHg to 500 mmHg $O_2$, 150 mmHg to 500 mmHg $O_2$, 200 mmHg to 500 mmHg $O_2$, 250 mmHg to 500 mmHg $O_2$, 300 mmHg to 500 mmHg $O_2$, 350 mmHg to 500 mmHg $O_2$, 400 mmHg to 500 mmHg $O_2$ or 450 mmHg to 500 mmHg $O_2$.

In some embodiments, administering oxygen in a stepwise manner includes administering oxygen in 20 mmHg increments in the range of any one or more of 30 mmHg to 100 mmHg $O_2$, 50 mmHg to 100 mmHg $O_2$, 70 mmHg to 100 mmHg $O_2$, 90 mmHg to 100 mmHg $O_2$, 30 mmHg to 200 mmHg $O_2$, 50 mmHg to 200 mmHg $O_2$, 70 mmHg to 200 mmHg $O_2$, 90 mmHg to 200 mmHg $O_2$, 150 mmHg to 200 mmHg $O_2$, 30 mmHg to 300 mmHg $O_2$, 50 mmHg to 300 mmHg $O_2$, 100 mmHg to 300 mmHg $O_2$, 150 mmHg to 300 mmHg $O_2$, 200 mmHg to 300 mmHg $O_2$, 200 mmHg to 300 mmHg $O_2$, 250 mmHg to 300 mmHg $O_2$, 30 mmHg to 400 mmHg $O_2$, 50 mmHg to 400 mmHg $O_2$, 100 mmHg to 400 mmHg $O_2$, 150 mmHg to 400 mmHg $O_2$, 200 mmHg to 400 mmHg $O_2$, 250 mmHg to 400 mmHg $O_2$, 300 mmHg to 400 mmHg $O_2$, 350 mmHg to 400 mmHg $O_2$, 30 mmHg to 500 mmHg $O_2$, 500 mmHg to 500 mmHg $O_2$, 100 mmHg to 500 mmHg $O_2$, 150 mmHg to 500 mmHg $O_2$, 200 mmHg to 500 mmHg $O_2$, 250 mmHg to 500 mmHg $O_2$, 300 mmHg to 500 mmHg $O_2$, 350 mmHg to 500 mmHg $O_2$, 400 mmHg to 500 mmHg $O_2$ or 450 mmHg to 500 mmHg $O_2$.

In some embodiments, administering oxygen in a stepwise manner includes administering oxygen in 30 mmHg increments in the range of any one or more of 30 mmHg to 100 mmHg $O_2$, 50 mmHg to 100 mmHg $O_2$, 70 mmHg to 100 mmHg $O_2$, 90 mmHg to 100 mmHg $O_2$, 30 mmHg to 200 mmHg $O_2$, 50 mmHg to 200 mmHg $O_2$, 70 mmHg to 200 mmHg $O_2$, 90 mmHg to 200 mmHg $O_2$, 150 mmHg to 200 mmHg $O_2$, 30 mmHg to 300 mmHg $O_2$, 50 mmHg to 300 mmHg $O_2$, 100 mmHg to 300 mmHg $O_2$, 150 mmHg to 300 mmHg $O_2$, 200 mmHg to 300 mmHg $O_2$, 200 mmHg to 300 mmHg $O_2$, 250 mmHg to 300 mmHg $O_2$, 30 mmHg to 400 mmHg $O_2$, 50 mmHg to 400 mmHg $O_2$, 100 mmHg to 400 mmHg $O_2$, 150 mmHg to 400 mmHg $O_2$, 200 mmHg to 400 mmHg $O_2$, 250 mmHg to 400 mmHg $O_2$, 300 mmHg to 400 mmHg $O_2$, 350 mmHg to 400 mmHg $O_2$, 30 mmHg to 500 mmHg $O_2$, 500 mmHg to 500 mmHg $O_2$, 100 mmHg to 500 mmHg $O_2$, 150 mmHg to 500 mmHg $O_2$, 200 mmHg to 500 mmHg $O_2$, 250 mmHg to 500 mmHg $O_2$, 300 mmHg to 500 mmHg $O_2$, 350 mmHg to 500 mmHg $O_2$, 400 mmHg to 500 mmHg $O_2$ or 450 mmHg to 500 mmHg $O_2$.

In some embodiments, administering oxygen in a stepwise manner includes administering oxygen in 40 mmHg increments in the range of any one or more of 30 mmHg to 100 mmHg $O_2$, 50 mmHg to 100 mmHg $O_2$, 70 mmHg to 100 mmHg $O_2$, 90 mmHg to 100 mmHg $O_2$, 30 mmHg to 200 mmHg $O_2$, 50 mmHg to 200 mmHg $O_2$, 70 mmHg to 200 mmHg $O_2$, 90 mmHg to 200 mmHg $O_2$, 150 mmHg to 200 mmHg $O_2$, 30 mmHg to 300 mmHg $O_2$, 50 mmHg to 300 mmHg $O_2$, 100 mmHg to 300 mmHg $O_2$, 150 mmHg to 300 mmHg $O_2$, 200 mmHg to 300 mmHg $O_2$, 200 mmHg to 300 mmHg $O_2$, 250 mmHg to 300 mmHg $O_2$, 30 mmHg to 400 mmHg $O_2$, 50 mmHg to 400 mmHg $O_2$, 100 mmHg to 400 mmHg $O_2$, 150 mmHg to 400 mmHg $O_2$, 200 mmHg to 400 mmHg $O_2$, 250 mmHg to 400 mmHg $O_2$, 300 mmHg to 400 mmHg $O_2$, 350 mmHg to 400 mmHg $O_2$, 30 mmHg to 500 mmHg $O_2$, 500 mmHg to 500 mmHg $O_2$, 100 mmHg to 500 mmHg $O_2$, 150 mmHg to 500 mmHg $O_2$, 200 mmHg to 500 mmHg $O_2$, 250 mmHg to 500 mmHg $O_2$, 300 mmHg to 500 mmHg $O_2$, 350 mmHg to 500 mmHg $O_2$, 400 mmHg to 500 mmHg $O_2$ or 450 mmHg to 500 mmHg $O_2$.

In some embodiments, administering oxygen in a stepwise manner includes administering oxygen in 50 mmHg increments in the range of any one or more of 30 mmHg to 100 mmHg $O_2$, 50 mmHg to 100 mmHg $O_2$, 70 mmHg to 100 mmHg $O_2$, 90 mmHg to 100 mmHg $O_2$, 30 mmHg to 200 mmHg $O_2$, 50 mmHg to 200 mmHg $O_2$, 70 mmHg to 200 mmHg $O_2$, 90 mmHg to 200 mmHg $O_2$, 150 mmHg to 200 mmHg $O_2$, 30 mmHg to 300 mmHg $O_2$, 50 mmHg to 300 mmHg $O_2$, 100 mmHg to 300 mmHg $O_2$, 150 mmHg to 300 mmHg $O_2$, 200 mmHg to 300 mmHg $O_2$, 200 mmHg to 300 mmHg $O_2$, 250 mmHg to 300 mmHg $O_2$, 30 mmHg to 400 mmHg $O_2$, 50 mmHg to 400 mmHg $O_2$, 100 mmHg to 400 mmHg $O_2$, 150 mmHg to 400 mmHg $O_2$, 200 mmHg to 400 mmHg $O_2$, 250 mmHg to 400 mmHg $O_2$, 300 mmHg to 400 mmHg $O_2$, 350 mmHg to 400 mmHg $O_2$, 30 mmHg to 500 mmHg $O_2$, 500 mmHg to 500 mmHg $O_2$, 100 mmHg to 500 mmHg $O_2$, 150 mmHg to 500 mmHg $O_2$, 200 mmHg to 500 mmHg $O_2$, 250 mmHg to 500 mmHg $O_2$, 300 mmHg to 500 mmHg $O_2$, 350 mmHg to 500 mmHg $O_2$, 400 mmHg to 500 mmHg $O_2$ or 450 mmHg to 500 mmHg $O_2$.

Other increments of carbon dioxide and oxygen to be administered in a stepwise manner will be readily apparent to a person having ordinary skill in the art.

In some embodiment, a predetermined combination of partial pressure of carbon dioxide and/or oxygen prior to re-establishing perfusion will be administered so as to adapt the subject for reperfusion. Block administration of carbon dioxide and/or oxygen comprises administering carbon dioxide and/or oxygen in alternating amounts over a period of time.

Alternating amounts of $CO_2$ comprises alternating between any of 20 mmHg and 40 mmHg, 30 mmHg and 40 mmHg, 20 mmHg and 50 mmHg, 30 mmHg and 50 mmHg, 40 mmHg and 50 mmHg, 20 mmHg and 60 mmHg, 30 mmHg and 60 mmHg, 40 mmHg and 60 mmHg, or 50 mmHg and 60 mmHg of carbon dioxide. In various embodiments, the predetermined levels of $CO_2$ are administered so that the arterial level of $CO_2$ reaches the $PaCO_2$ of any one or more of the above ranges. Other amounts of carbon dioxide to be used in alternating amounts over a period of time will be readily apparent to a person having ordinary skill in the art.

Alternating amounts of $O_2$ comprises alternating between any of 5 mmHg and 100 mgHg, 20 mmHg and 100 mmHg, 30 mmHg and 100 mmHg, 40 mmHg and 100 mmHg, 50 mmHg and 100 mmHg, 60 mmHg and 100 mmHg, 70 mmHg and 100 mmHg, 80 mmHg and 100 mmHg, 90 mmHg and 100 mmHg, 20 mmHg and 40 mmHg, 30 mmHg and 40 mmHg, 20 mmHg and 50 mmHg, 30 mmHg and 50 mmHg, 40 mmHg and 50 mmHg, 20 mmHg and 60 mmHg, 30 mmHg and 60 mmHg, 40 mmHg and 60 mmHg, or 50 mmHg and 60 mmHg of oxygen. In various embodiments, the predetermined levels of $O_2$ is administered so that the arterial level of $O_2$ reaches the $PaO_2$ of any one or more of the above ranges. Other amounts of oxygen to be used in alternating amounts over a period of time will be readily apparent to a person having ordinary skill in the art.

EXAMPLES

Example 1

Canines (n=9) underwent left thoracotomy at the $4^{th}$ intercostal space and a hydraulic occluder was secured around the left-anterior descending coronary artery after the first principal diagonal. Subsequently a Doppler flow probe was affixed distal to the hydraulic occluder and animals were allowed to recover for 7 days. Following recovery, animals were subjected to ischemia/reperfusion (I/R) protocol and studied with magnetic resonance imaging. The ischemia protocol consisted of inflicting no-flow ischemia by inflating the hydraulic occlude (confirmed by the Doppler flow velocity) for 3 hours. Subsequently all animals were reperfused by deflation of the hydraulic occluder. During ischemia all animals were intubated and mechanically ventilated with ventilator with 100% $O_2$. In a fraction the animals (n=5), during reperfusion the ventilation with 100% $O_2$ was maintained, while remainder of the animals (n=4) were allowed to breathe room air.

Animals were imaged on a 3.0 T Siemens MRI system and left-ventricular ejection fraction and scar volume as a percentage of the left ventricular volume were computed at week 8, post I/R injury, based on previously published methods[1,4].

TABLE 1

|  | Scar Volume at week 8 post MI (% LV) | LVEF at week 8 post MI |
|---|---|---|
| Animals breathing 100% $O_2$ during reperfusion | 15.0 +/− 3.8 | 39.7 +/− 4.9 |
| Animals breathing room air during reperfusion | 11.2 +/− 3.6 | 45.2 +/− 3.6 |

These results show that animals receiving 100% $O_2$ during reperfusion had worse outcomes (larger scar size) and poorer remodeling (lower ejection fraction) than those animals breathing room air during reperfusion. In particular, these studies showed that the chronic scar size was approximately 25% larger and the left ventricular ejection fraction (LVEF) was reduced by 12% in animals receiving 100% $O_2$ versus those that were breathing room air during the reperfusion.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

REFERENCES

1. Can J C, Simonetti O, Bundy J, Li D, Pereles S, Finn J P. Cine M R angiography of the heart with segmented true fast imaging with steady-state precession. Radiology. 2001 June; 219(3):828-34.
2. Kachenoura N, Redheuil A, Balvay D, Ruiz-Dominguez C, Herment A, Mousseaux E, Frouin F. Evaluation of regional myocardial function using automated wall motion analysis of cine MR images: Contribution of parametric images, contraction times, and radial velocities. J Magn Reson Imaging. 2007 October; 26(4):1127-32.
3. Abdel-Aty, H., et al., Delayed enhancement and T2-weighted cardiovascular magnetic resonance imaging differentiate acute from chronic myocardial infarction. Circulation, 2004. 109(20): p. 2411-6.

4. Kim R J, Fieno D S, Parrish T B, et al. Relationship of MRI delayed contrast enhancement to irreversible injury, infarct age, and contractile function. Circulation 1999; 100(19): 1992-2002.

What is claimed is:

1. A method for reducing or inhibiting ischemia-reperfusion injury in a subject in need thereof comprising:
   (i) administering to the subject a first admixture comprising carbon dioxide in an amount to reach a predetermined partial pressure of carbon dioxide to induce hyperemia;
   (ii) administering to the subject a second admixture comprising oxygen in an amount to reach a predetermined partial pressure of oxygen;
   (iii) administering oxygen in a block-wise manner to the subject prior to re-establishing perfusion so as to adapt the subject for reperfusion, wherein administering oxygen in a block-wise manner comprises alternating the amounts of oxygen administered between any of 5 mmHg and 100 mgHg, 20 mmHg and 100 mmHg, 30 mmHg and 100 mmHg, 40 mmHg and 100 mmHg, 50 mmHg and 100 mmHg, 60 mmHg and 100 mmHg, 70 mmHg and 100 mmHg, 80 mmHg and 100 mmHg, 90 mmHg and 100 mmHg, 20 mmHg and 40 mmHg, 30 mmHg and 40 mmHg, 20 mmHg and 50 mmHg, 30 mmHg and 50 mmHg, 40 mmHg and 50 mmHg, 20 mmHg and 60 mmHg, 30 mmHg and 60 mmHg, 40 mmHg and 60 mmHg, or 50 mmHg and 60 mmHg of oxygen; and
   (iv) re-establishing perfusion to an ischemic area, so as to reduce or inhibit ischemia-reperfusion injury in the subject.

2. The method of claim 1, further comprising establishing therapeutic hypothermia by cooling blood prior to reperfusion.

3. The method of claim 2, wherein therapeutic hypothermia is established via surface cooling or via the use of a catheter through the femoral artery.

4. The method of claim 2, wherein the blood is cooled to 2-7° C. lower than the normal systemic temperature.

5. The method of claim 1, further comprising administering carbon dioxide in a block-wise manner to the subject prior to re-establishing perfusion so as to adapt the subject for reperfusion.

6. The method of claim 5, wherein administering carbon dioxide in a block-wise manner comprises alternating the amounts of carbon dioxide administered between any of 20 mmHg and 40 mmHg, 30 mmHg and 40 mmHg, 20 mmHg and 50 mmHg, 30 mmHg and 50 mmHg, 40 mmHg and 50 mmHg, 20 mmHg and 60 mmHg, 30 mmHg and 60 mmHg, 40 mmHg and 60 mmHg, or 50 mmHg and 60 mmHg.

7. The method of claim 1, further comprising monitoring reperfusion injury or microvascular obstructions using magnetic resonance imaging during reperfusion and post-reperfusion.

8. The method of claim 1, wherein perfusion is re-established using any one or more of fibrinolytic therapy, angioplasty or CABG.

9. The method of claim 8, wherein the first and second admixtures are administered before, during and/or after re-establishing perfusion.

10. The method of claim 1, wherein the first and second admixtures are administered concurrently.

11. The method of claim 1, wherein the first and second admixtures are administered sequentially.

12. The method of claim 1, wherein the subject has ischemic heart disease or myocardial ischemia.

13. A method for reducing microvascular obstructions in a subject in need thereof comprising:
   (i) administering to the subject a first admixture comprising carbon dioxide in an amount to reach a predetermined partial pressure of carbon dioxide to induce hyperemia;
   (ii) administering to the subject a second admixture comprising oxygen in an amount to reach a predetermined partial pressure of oxygen;
   (iii) administering oxygen in a block-wise manner to the subject prior to re-establishing perfusion so as to adapt the subject for reperfusion, wherein administering oxygen in a block-wise manner comprises alternating the amounts of oxygen administered between any of 5 mmHg and 100 mgHg, 20 mmHg and 100 mmHg, 30 mmHg and 100 mmHg, 40 mmHg and 100 mmHg, 50 mmHg and 100 mmHg, 60 mmHg and 100 mmHg, 70 mmHg and 100 mmHg, 80 mmHg and 100 mmHg, 90 mmHg and 100 mmHg, 20 mmHg and 40 mmHg, 30 mmHg and 40 mmHg, 20 mmHg and 50 mmHg, 30 mmHg and 50 mmHg, 40 mmHg and 50 mmHg, 20 mmHg and 60 mmHg, 30 mmHg and 60 mmHg, 40 mmHg and 60 mmHg, or 50 mmHg and 60 mmHg of oxygen; and
   (iv) re-establishing perfusion to an ischemic area, so as to reduce microvascular obstructions in the subject.

14. The method of claim 13, further comprising establishing therapeutic hypothermia by cooling blood prior to reperfusion.

15. The method of claim 13, further comprising administering carbon dioxide in a block-wise manner to the subject prior to re-establishing perfusion so as to adapt the subject for reperfusion.

16. The method of claim 13, further comprising monitoring reperfusion injury or microvascular obstructions using magnetic resonance imaging during reperfusion and post-reperfusion.

17. A method for reducing hemorrhagic microvascular obstructions in a subject in need thereof comprising:
   (i) administering to the subject a first admixture comprising carbon dioxide in an amount to reach a predetermined partial pressure of carbon dioxide to induce hyperemia;
   (ii) administering to the subject a second admixture comprising oxygen in an amount to reach a predetermined partial pressure of oxygen;
   (iii) administering oxygen in a block-wise manner to the subject prior to re-establishing perfusion so as to adapt the subject for reperfusion, wherein administering oxygen in a block-wise manner comprises alternating the amounts of oxygen administered between any of 5 mmHg and 100 mgHg, 20 mmHg and 100 mmHg, 30 mmHg and 100 mmHg, 40 mmHg and 100 mmHg, 50 mmHg and 100 mmHg, 60 mmHg and 100 mmHg, 70 mmHg and 100 mmHg, 80 mmHg and 100 mmHg, 90 mmHg and 100 mmHg, 20 mmHg and 40 mmHg, 30 mmHg and 40 mmHg, 20 mmHg and 50 mmHg, 30 mmHg and 50 mmHg, 40 mmHg and 50 mmHg, 20 mmHg and 60 mmHg, 30 mmHg and 60 mmHg, 40 mmHg and 60 mmHg, or 50 mmHg and 60 mmHg of oxygen; and
   (iv) re-establishing perfusion to an ischemic area, so as to reduce hemorrhagic microvascular obstructions in the subject.

18. The method of claim 17, further comprising establishing therapeutic hypothermia by cooling blood prior to reperfusion.

19. The method of claim 17, further comprising administering carbon dioxide in a block-wise manner to the subject prior to re-establishing perfusion so as to adapt the subject for reperfusion.

20. The method of claim 17, further comprising monitoring reperfusion injury or microvascular obstructions using magnetic resonance imaging during reperfusion and post-reperfusion.

* * * * *